US006729185B2

(12) United States Patent
Autrey et al.

(10) Patent No.: US 6,729,185 B2
(45) Date of Patent: May 4, 2004

(54) PHOTOACOUSTIC SAMPLE VESSEL AND METHOD OF ELEVATED PRESSURE OPERATION

(75) Inventors: Tom Autrey, West Richland, WA (US); Clement R. Yonker, Kennewick, WA (US)

(73) Assignee: Battelle Memorial Institute, Richland, WA (US)

( * ) Notice: Subject to any disclaimer, the term of this patent is extended or adjusted under 35 U.S.C. 154(b) by 33 days.

(21) Appl. No.: 09/766,251

(22) Filed: Jan. 19, 2001

(65) Prior Publication Data

US 2002/0026833 A1 Mar. 7, 2002

Related U.S. Application Data

(63) Continuation-in-part of application No. 09/277,687, filed on Mar. 26, 1999, now abandoned.

(51) Int. Cl.$^7$ .............................................. G01N 29/22
(52) U.S. Cl. .................. 73/643; 73/64.53; 356/432; 250/339.1
(58) Field of Search ................. 73/587, 64.53, 73/643, 64.56, 570, 24.02, 24.06; 356/432, 440, 436, 369; 250/241.1, 343, 339.1

(56) References Cited

U.S. PATENT DOCUMENTS

| | | | | |
|---|---|---|---|---|
| 4,184,768 A | * | 1/1980 | Murphy et al. | 356/326 |
| 4,276,780 A | * | 7/1981 | Patel et al. | 356/432 |
| 4,436,428 A | | 3/1984 | Watanabe et al. | 356/432 |
| 4,818,882 A | * | 4/1989 | Nexo et al. | 356/432 |
| 5,444,541 A | * | 8/1995 | Small et al. | 356/432 |
| 5,596,146 A | * | 1/1997 | Waller et al. | 356/432 |
| 5,913,234 A | | 6/1999 | Julliard et al. | 73/24.02 |
| 6,236,455 B1 | * | 5/2001 | Autrey et al. | 356/432 |
| 6,244,101 B1 | * | 6/2001 | Autrey et al. | 356/432 |

FOREIGN PATENT DOCUMENTS

JP  62 228140 A  10/1987

OTHER PUBLICATIONS

Patent Abstracts of Japan vol. 012, No. 095(p–681)., Mar. 29, 1988, Toshiba Corp.

T Autrey et al., "Nanojoules, Nanoliters, and Nanosecond Calorimetry", p. 13–19. 1999.

EF Walsch et al., "Energetics of the Reactions of $(\eta^6–C_6H_6)Cr(CO)_3$ with n–Heptane, $N_2$, and $H_2$, Studied by High Pressure Photoacoustic Calorimetry", p. 19425–19429. 1996.

EF Walsch et al., "Photoacoustic Calorimetry at High Pressure: A New Approach to Determination of Bond Strengths", 12016–12020. 1995.

\* cited by examiner

*Primary Examiner*—Hezron Williams
*Assistant Examiner*—Nashmiya Fayyaz
(74) *Attorney, Agent, or Firm*—Stephen R. May; Douglas E. McKinley, Jr.

(57) ABSTRACT

An improved photoacoustic vessel and method of photoacoustic analysis. The photoacoustic sample vessel comprises an acoustic detector, an acoustic couplant, and an acoustic coupler having a chamber for holding the acoustic couplant and a sample. The acoustic couplant is selected from the group consisting of liquid, solid, and combinations thereof. Passing electromagnetic energy through the sample generates an acoustic signal within the sample, whereby the acoustic signal propagates through the sample to and through the acoustic couplant to the acoustic detector.

12 Claims, 7 Drawing Sheets

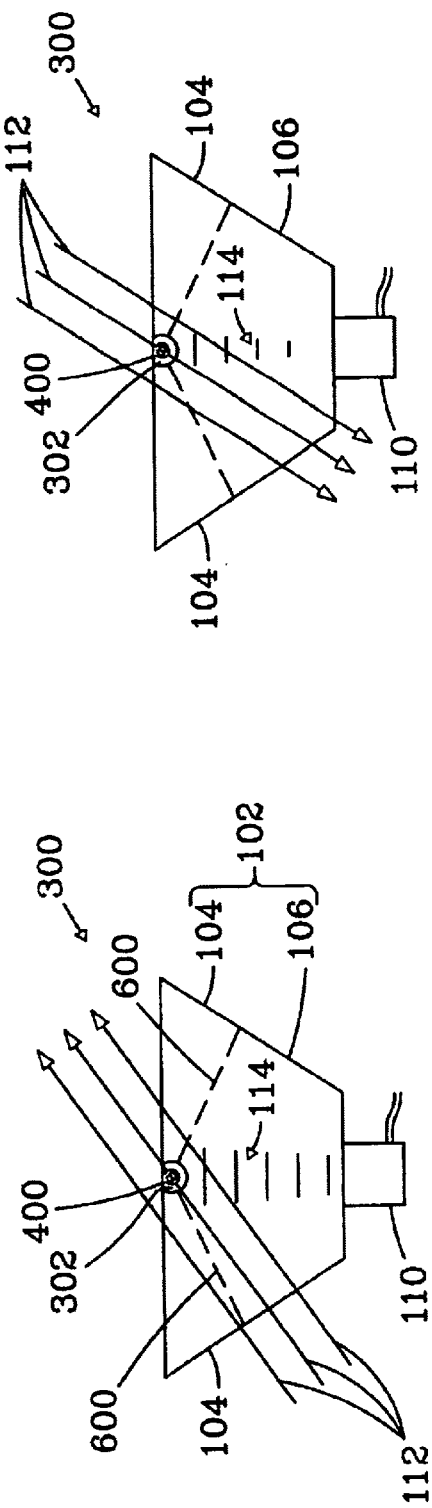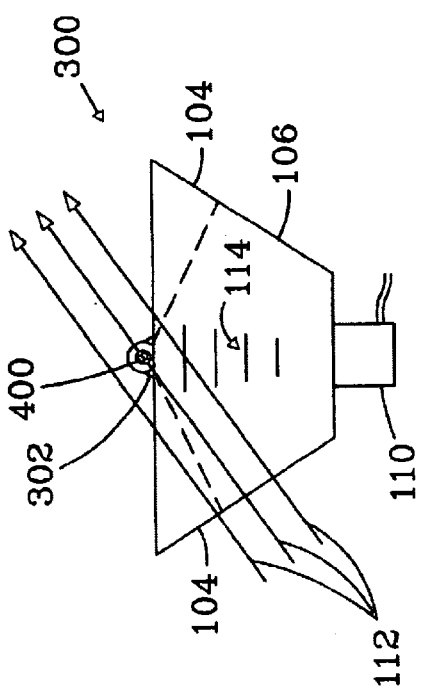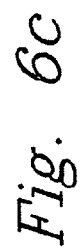

PHOTOACOUSTIC SAMPLE VESSEL AND METHOD OF ELEVATED PRESSURE OPERATION

CROSS REFERENCES TO RELATED APPLICATIONS

This application is a continuation-in-part of application Ser. No. 09/277,687 filed Mar. 26, 1999 now abandoned.

STATEMENT REGARDING FEDERALLY SPONSORED RESEARCH AND DEVELOPMENT

This invention was made with Government support under Contract DE-AC0676RL01830 awarded by the U.S. Department of Energy. The Government has certain rights in the invention.

FIELD OF THE INVENTION

The present invention relates to photoacoustic analysis of a sample using a photoacoustic sample vessel. As used herein, the sample is a material that may be a gas, liquid, solid, or combination thereof including supercritical fluid, slurry, and suspension.

BACKGROUND OF THE INVENTION

Photoacoustic or optoacoustic methods are used as a tool in many applications to obtain chemical and physical information on the properties of materials in solution, solids, or gases. Absorption of irradiation, for example electromagnetic, by a material generates an electronically/vibrationally-excited state intermediate. Several channels of excited state "deactivation" lead to an observable photoinduced acoustic signal including (1) heat released from the excited state as it relaxes back to the ground state, (2) volume changes in the material due to absorption of light, and/or (3) electrostriction of the media surrounding the material due to polar changes in the excited state.

All three phenomena of heat, volume, and electrostriction generate an acoustic wave that is typically detected with a piezoelectric transducer. A photoacoustic vessel couples the light into the material and couples the resulting acoustic wave to the transducer.

Referring to FIG. 1, a typical photoacoustic vessel 100 comprises an acoustic detector 110 and an acoustic coupler 102 (usually known as a cuvette) that provides a chamber for holding a sample 108. The acoustic coupler 102 has a first body 104 (vertical sides or walls) and a second body 106 (bottom). The first body 104 cooperates with the second body 106 (by being attached) to form the chamber. The acoustic detector 110 is mounted on the second body 106. Thus, upon introduction of electromagnetic energy 112, for example light, an acoustic signal 114 is generated within the sample 108 and propagates through the sample 108 into and through the acoustic coupler 102 to the acoustic detector 110.

A disadvantage of the cuvette type photoacoustic vessel is a requirement for a relatively large volume (milliliters) of sample 108 required to perform the measurement. Specifically, in the life sciences fields, new biological samples may be extremely expensive or difficult to obtain, synthesize, or purify. Thus, there is a need for photoacoustic vessels having smaller sample volumes for obtaining important data. Another disadvantage of this technique is the limitation of the sample 108 being at atmospheric pressure due to the chamber provided by the cuvette being open to the environment.

FIG. 2 illustrates an improved photoacoustic vessel 100' described in U.S. patent application Ser. No. 09/105,781 now U.S. Pat. No. 6,236,455, filed Jun. 26, 1998, incorporated by reference herein to the extent not inconsistent with the disclosure herewith. The photoacoustic vessel 100' comprises an acoustic detector 110 and an acoustic coupler 102' (referred to as a prism cell) that provides an enclosed chamber for holding a sample 108. The acoustic coupler 102' has a first body 104 and a second body 106 with a shim 200 or spacer therebetween defining the chamber containing the sample 108. The shim 200 contacts a perimeter of the first and second bodies 104,106 as shown thereby forming a perimeter wall(s). The first body 104 forms a first wall of the chamber and the second body 106 forms a second wall of the chamber. The second body 106 has an acoustic detector 110 mounted thereon. Thus, upon introduction of electromagnetic energy (e.g., light) 112 an acoustic signal 114 is generated within the sample 108 and propagates through the sample 108 into and through the second body 106 to the acoustic detector 110. Sample volumes of less than 1 ml and as low as 0.1 ml have been achieved with this device.

High-pressure time-resolved photoacoustic studies have been done and obtained results for the kinetics of photogenerated meta-stable intermediates ([a] E. F. Walsh, M. W. George, S. Goff, S. M. Nikiforov, V. K. Popov, X.-Z. Sun, and M. Poliakoff, Energetics of the Reactions of $(n_6\text{-}C_6H_6)$ $Cr(CO)_3$ with n-Heptane, $N_2$, and $H_2$ Studied by High-Pressure Photoacoustic Calorimetry, *J. Phys. Chem.*, 100 (1996) 19425–19429; [b] E. F. Walsh, V. K. Popov, M. W. George, and M. Poliakoff, Photoacoustic Calorimetry at High Pressure: A New Approach to Determination of Bond Strengths. Estimation of the M—L Bond Dissociation Energy of $M(CO)_5L$ (M=Cr, Mo; L=$H_2$, $N_2$) in n-Heptane Solution, *J. Phys. Chem.*, 99 (1995) 12016–20). Pressures up to 130 bar (2000 psi) were reported. In addition to the upper pressure limitation, these systems were not conducive to obtaining time-resolved data, limited to optically dense samples, and had no flow-through capability.

Thus, in spite of these advances, there continue to be applications requiring yet smaller sample volumes (e.g., nanoliters). In addition, because photoacoustic methods generally are highly sensitive but have low selectivity, there remains a need for obtaining dynamic photoacoustic data to enhance the selectivity of the opto- or photo-acoustic technique.

BRIEF SUMMARY OF THE INVENTION

The present invention is an improved photoacoustic vessel and method of photoacoustic analysis. The photoacoustic sample vessel comprises an acoustic detector, an acoustic couplant, and an acoustic coupler having a chamber for holding the acoustic couplant and a sample. The acoustic couplant is selected from the group consisting of liquid, solid, and combinations thereof. Passing electromagnetic energy through the sample generates an acoustic signal within the sample, whereby the acoustic signal propagates through the sample to and through the acoustic couplant to the acoustic detector.

In another embodiment of the present invention, the photoacoustic sample vessel further comprises a sample container, wherein the sample is contained within the sample container and the acoustic signal propagates through the sample into and through the wall of the container into and through the acoustic couplant to the acoustic detector.

In another embodiment of the present invention, the sample is pressurized above atmospheric pressure.

It is an object of the present invention to provide a photoacoustic sample vessel that uses a small sample volume.

It is a further object of the present invention to provide a method of photoacoustic analysis of samples at elevated pressure.

It is a further object of the present invention to provide a method of dynamic photoacoustic analysis.

An advantage of the present invention is the ability to use substantially reduced sample volume needed for a photoacoustic measurement. Specifically, the present invention is capable of using a sample volume of less than 0.1 ml and as low as a few nanoliters. An additional advantage is the capability to perform measurements under elevated pressures as great as 60,000 psi. Further, it is possible to obtain time-resolved data (dynamic signal analysis for greater selectivity) with the present invention. Analysis of the shape of the acoustic waveform provides the selectivity while analysis of the amplitude provides the sensitivity.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

BRIEF DESCRIPTION OF THE DRAWINGS

FIG. 6a is a cross section view through the centerline of a prism cell type photoacoustic sample vessel having a sample container in a channel and with an acoustic detector mounted on the acoustic coupler according to the present invention.

FIG. 6b is a cross section view through the centerline of the photoacoustic sample vessel of FIG. 6a with a reversed electromagnetic energy direction.

FIG. 6c is a cross section view through the centerline of a prism cell type photoacoustic sample vessel having a sample container without a channel and with an acoustic detector mounted on the acoustic coupler according to the present invention.

FIG. 7b is a first section view of FIG. 7a.

FIG. 7c is a second section view of FIG. 7a.

DETAILED DESCRIPTION OF THE INVENTION

Figure 1:
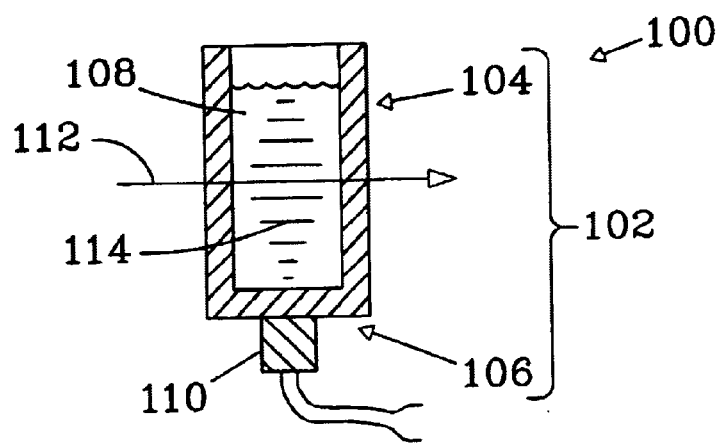
FIG. 1 is a cross section view through the centerline of a prior art cuvette type photoacoustic vessel.
Figure 2:
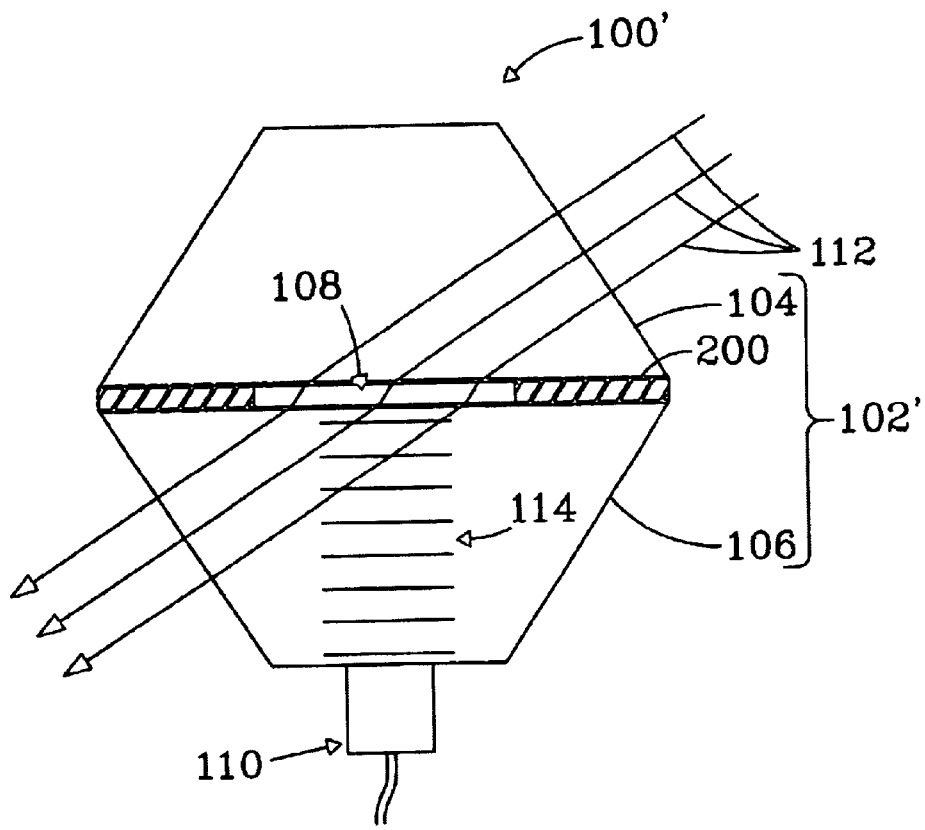
FIG. 2 is a cross section view through the centerline of a prism cell type photoacoustic vessel.
Figure 3A:
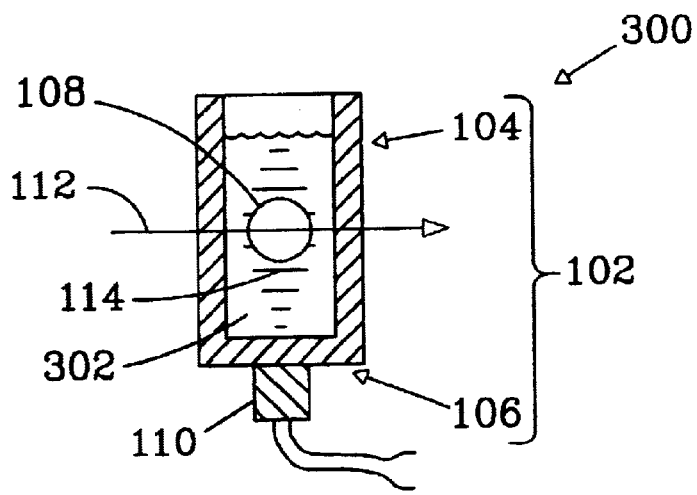
FIG. 3a is a cross section view through the centerline of a cuvette type photoacoustic sample vessel with an acoustic detector mounted on the acoustic coupler according to the present invention.

The present invention is an improved photoacoustic sample vessel and method of photoacoustic analysis. As illustrated in FIG. 3a, the photoacoustic sample vessel 300 of the present invention comprises an acoustic detector 110, an acoustic couplant 302, and an acoustic coupler 102 having a chamber for holding the acoustic couplant 302 and a sample 108. The acoustic couplant 302 is selected from the group consisting of liquid, solid, and combinations thereof. Passing electromagnetic energy 112 through the sample 108 generates an acoustic signal 114 within the sample 108, whereby the acoustic signal 114 propagates through the sample 108 into and through the acoustic couplant 302, into and through the acoustic coupler 102 to the acoustic detector 110.

Figure 3B:
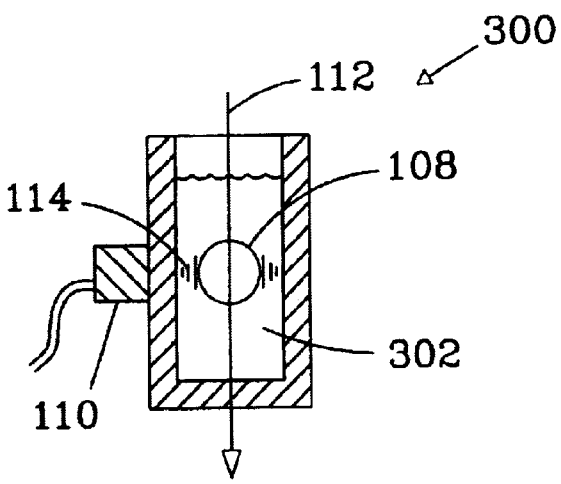
FIG. 3b is a cross section view through the centerline of a cuvette type photoacoustic sample vessel, similar to that of FIG. 3a, except that the electromagnetic energy comes from a different direction and the acoustic detector is mounted on the acoustic coupler in a different location.

FIG. 3b illustrates another embodiment of the present invention whereby the acoustic detector 110 is mounted on the acoustic coupler 102 at a different location and the electromagnetic energy 112 passes through the sample 108 from a different direction.

Figure 3C:
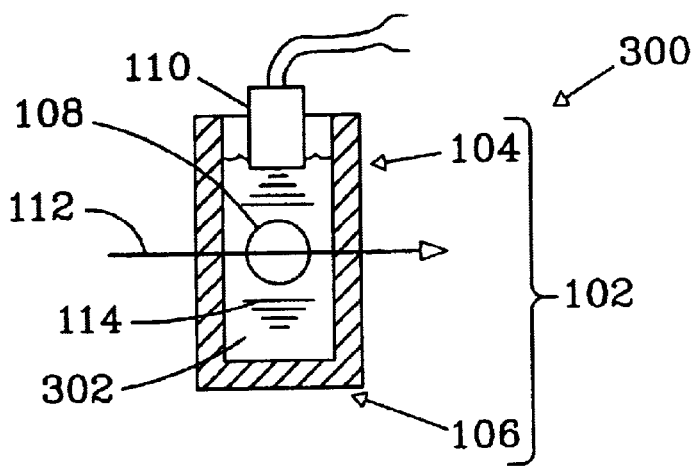
FIG. 3c is a cross section view through the centerline of a cuvette type photoacoustic sample vessel with an acoustic detector in contact with the acoustic couplant according to the present invention.

FIG. 3c illustrates another embodiment of the present invention whereby the acoustic detector 110 is in direct contact with the acoustic couplant 302. In this embodiment, passing electromagnetic energy 112 through the sample 108 generates an acoustic signal 114 within the sample 108, whereby the acoustic signal 114 propagates through the sample 108 into and through the acoustic couplant 302 directly to the acoustic detector 110.

In the embodiments of FIGS. 3a–c, there is no physical container between the sample 108 and acoustic couplant 302. Containment of the sample 108 to allow photoacoustic analysis of the sample 108 while it is in the acoustic couplant 302 may be achieved by a variety of methods known to one skilled in the art. For example, an acoustic couplant 302 that is immiscible in the sample 108 or that has a density different than that of the sample 1108 may be selected.

Figure 4:
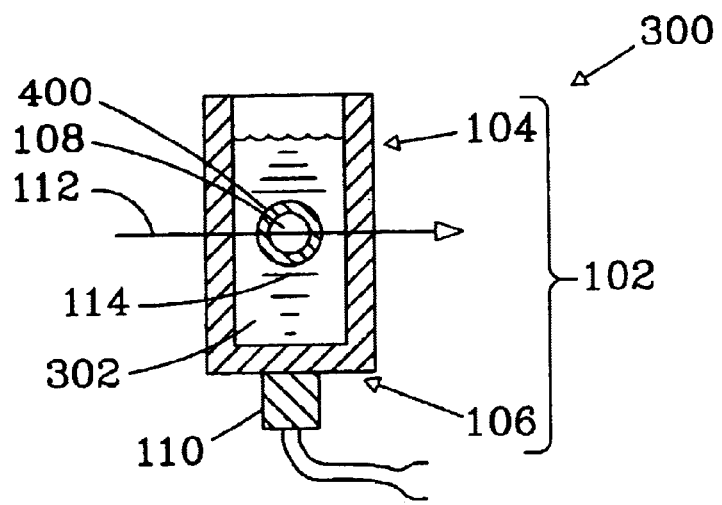
FIG. 4 is a cross section view through the centerline of a cuvette type photoacoustic sample vessel having a sample container with an acoustic detector mounted on the acoustic coupler according to the present invention.
Figure 5:
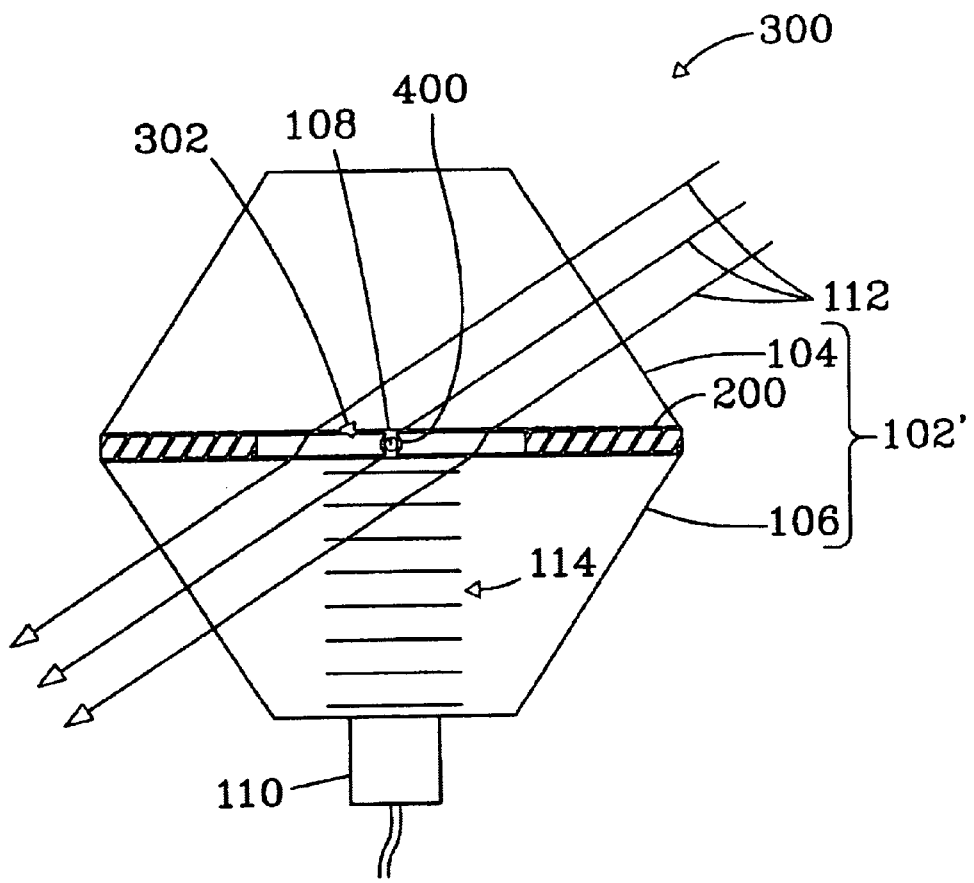
FIG. 5 is a cross section view through the centerline of a prism cell type photoacoustic sample vessel having a sample container with an acoustic detector mounted on the acoustic coupler according to the present invention.

FIGS. 4–5 illustrate further embodiments of the present invention whereby the sample 108 is contained within a sample container 400 and the acoustic signal 114 propagates through the sample 108 into and through the wall of the sample container 400 into and through the acoustic couplant 302 to the acoustic detector 110.

It will be apparent to one skilled in the art of photoacoustic analysis that the shape of the chamber provided by the acoustic coupler 102, 102' may be any shape convenient for passing electromagnetic energy 112 and receiving acoustic signals 114 with an acoustic detector 110. FIGS. 6a–c further exemplify other embodiments of the present invention whereby the first body 104 and second body 106 are distinguished on the basis of an arbitrary line 600 that passes from the position of the sample container 400 toward an outer surface of the acoustic coupler 102. In FIG. 6a, a chamber is provided for the sample 108, sample container 400, and acoustic couplant 302 by a channel in the acoustic coupler 102. FIG. 6b illustrates the embodiment of FIG. 6a except that the electromagnetic energy 112 passes through the sample 108 in the sample container 400 from a different direction. In FIG. 6c, the chamber is a flat surface whereupon rests the sample container 400 in the acoustic couplant 302.

The sample container 400 may be of any shape or material conducive to passing electromagnetic energy 112 and an acoustic signal 114. The sample container 400 may be fully enclosed within the chamber provided by the acoustic coupler 102, 102' or the sample container 400 may have a portion extending beyond the chamber. A preferred sample container 400 material is glass, for example quartz glass, most preferably fused silica. The preferred sample container 400 material is compatible with electromagnetic energy from ultraviolet through infrared including the visible spectrum.

Figure 7A:
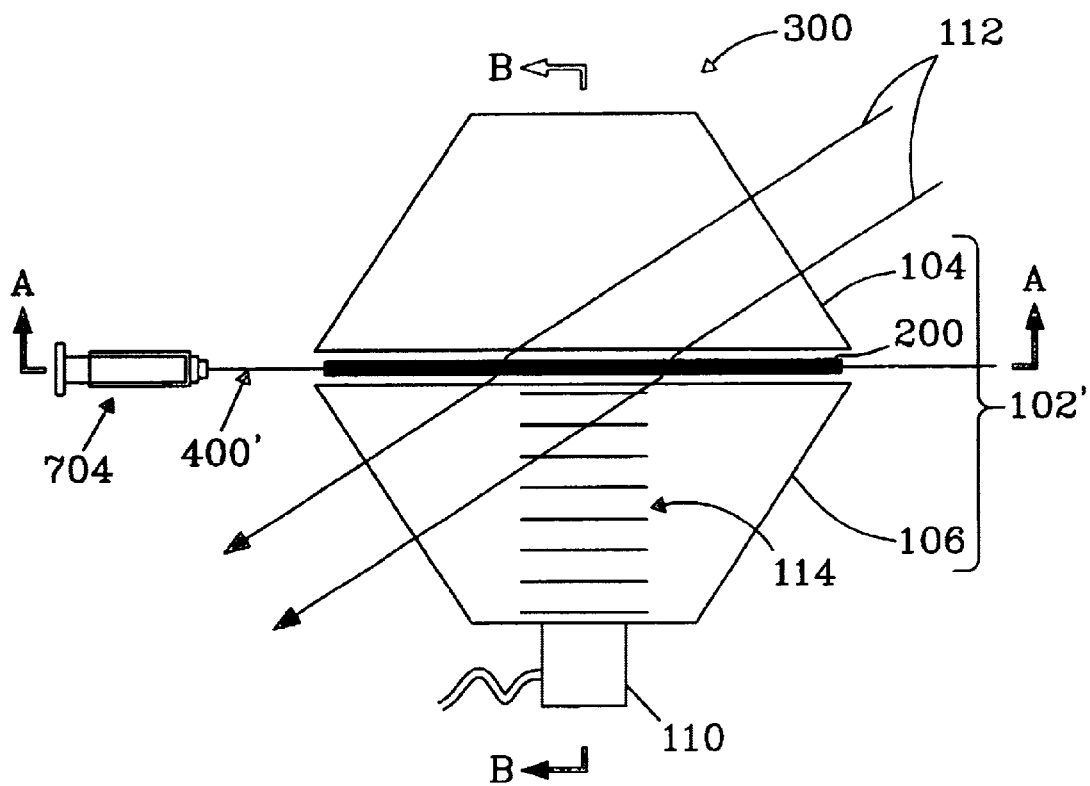
FIG. 7a is a cross section view through the centerline of a prism cell type photoacoustic sample vessel having a capillary tube as the sample container.
Figure 7B:
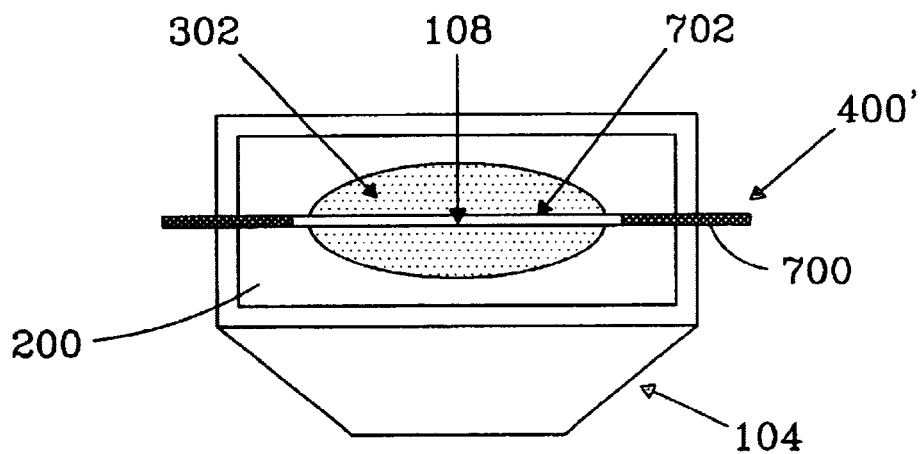
Figure 7C:
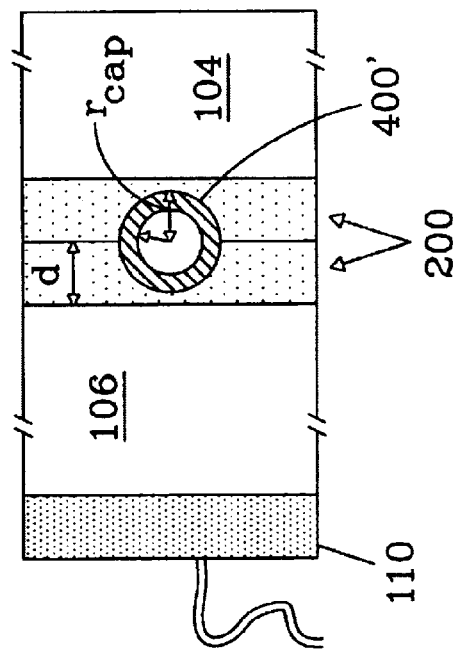

Another embodiment of the present invention comprises the sample container 400 comprising a capillary tube 400' as shown in FIGS. 7a–c. Such a sample container 400 design provides the capability of flowing the sample 108 through the photoacoustic sample vessel 300. Because capillary tubes 400' are normally provided with a polyamide coating 700, and because the polyamide coating 700 may interfere with either the electromagnetic energy 112 or the acoustic signal 114, or both, it is preferred to remove the polyamide coating from a portion 702 of the capillary tube 400' that is within the chamber. Use of a capillary tube 400' as the sample container 400 has the advantages of small sample volume and the ability to pressurize the sample 108 above atmospheric pressure, preferably above 1000 atmospheres, more preferably above 2000 atmospheres up to about 4000 atmospheres (60,000 psi) which is below the burst limit of capillary tubes 400' having an inside diameter of 100–180 $\mu$m and an outside diameter of 360 $\mu$m. It will be apparent to one skilled in the art that the sample 108 volume of the present invention may be equal to or less than, preferably much less than, the sample volume of the prior art and retains the advantage of elevated pressure capability as well as dynamic signal analysis.

As shown in FIG. 7c the sample container 400, 400' may be placed in between a pair of shims 200 each having a thickness d, for example 762 $\mu$m. The capillary tube 400' outside radius is shown as $r_{cap}$, for example 90 $\mu$m. The shim(s) 200 may be any material that has a compressive strength to maintain the chamber. In circumstances where it is desired that the sample container 400, 400' penetrate the acoustic coupler 102' as shown, the shim(s) 200 must have sufficient flexibility to conform and fluidically seal the outer surface of the sample container 400, 400'. Shim 200 material is any material that forms a seal including but is not limited to metal, polymer, for example Kalrez, and combinations thereof. A polymer, especially Kalrez, is preferred.

A sample container 400 is considered a capillary tube 400' when it is able to retain liquid water with both ends open so that the water is retained therein by surface tension. Larger sample containers 400 may be used but would require additional sample volume and may have lower pressure burst limit.

The choice of the acoustic couplant 302 in acoustic contact with the sample container 400 includes consideration of both low electromagnetic absorption at the excitation wavelength and the ability to transmit acoustic energy efficiently. The acoustic couplant 302 may be a liquid, solid, or combination thereof (e.g., a suspension or slurry). Liquid includes but is not limited to an organic liquid, such as a hydrocarbon, for example benzene, or an inorganic liquid, for example water. In many cases water is preferred because it has the ability to transmit acoustic energy efficiently. Water is also less costly and environmentally benign. Solid includes but is not limited to polymer, glass, and combinations thereof. The solid may begin in the form of a powder that is placed between the sample container 400 and the walls of the chamber. The powder is subsequently heated and fused or melted then cooled to a solid. The solid may also be a room temperature curing material for example epoxy. It is preferred to match the optical and acoustic properties of the acoustic couplant 302 and the acoustic coupler 102, 102' as nearly as possible for maximum signal to noise ratio.

Material and Equipment for Examples

Sample 108. The solvents, reagent grade, were obtained from Aldrich and used as received. Benzophenone (Bp) and o-hydroxybenzophenone (OHB) were obtained from Aldrich and then recrystallized from methanol for use as the sample 108.

Two sets of solutions containing (1) benzophenone and (2) OHB were prepared in acetonitrile. Both solutions were diluted with a second stock water solution containing potassium iodide (KI) to yield a set of samples 108 containing equivalent concentration of potassium iodide (KI) and maintaining matching optical densities (0.4 mm$^{-1}$) with a solvent composition of 9/1 acetonitrile/water. The samples were purged with nitrogen and charged into a gas tight 1000 mL syringe. Two to three data sets of data (R-wave (OHB), S-wave (Bp) and Background (KI/acetonitrile/water)) were collected at each KI concentration between 1 and 8 mM.

Sample Container 400. The sample container 400 was a capillary tube 400' of quartz having 180 $\mu$m ID and a cross sectional area of about 0.025 mm$^2$. The excitation volume ($V_o$) in the quenching experiments is thus about 100 nanoliters for a 4 mm length.

Preparation of the capillary tube 400' required pyrolysis of about 1 cm of the polyamide coating 700 on the 50 cm total length of the capillary tube 400' to provide an optically transparent portion 702.

Excitation Sources, Detectors, and Electronics. The electromagnetic energy was laser light as the fundamental line of a Nd:Yag laser (Continuum, Surelite, Santa Clara Calif.) was passed through a third harmonic generator to produce 355 nm light (15 ns FWHM, 10 Hz). An excimer laser (Lambda Physik, XeCl, Ft. Lauderdale Fla.) provided 308 nm light (20 ns FWHM, 5 Hz). Laser energies were measured with a energy meter (Scientech, #P09 joulemeter, Boulder Colo.).

The acoustic detector 110 for the photoacoustic signal was a 0.25 inch diameter, 5 MHz piezoelectric transducer (Panametrics, #A110S, Waltham Mass.). The detector output signal was amplified 100 times and averaged for 20–50 laser pulses. The detected signal was amplified (Panametrics, #5670, 100× gain, or a Stanford Research Systems, #240, 5, 25, 125× gain, Sunnyvale Calif.) and collected using a digitizing oscilloscope (Lecroy, Chestnut Ridge N.Y.). Deconvolution of the experimentally acquired acoustic waveforms was accomplished using Sound Analysis 3000 (Quantum Northwest, Spokane Wash.).

Photoacoustic Sample Vessel 300. The acoustic coupler 102' was as shown in FIGS. 7a–c. The sample container 400 was a capillary tube 400' (Polymicro Technologies, 360 mm OD, 180 and 100 mm ID, Phoenix Ariz.). The shim 200 was two Kalrez shims (Air Oil Products, Dupont #503N, Seattle Wash.) having a thickness of 0.030" to compress the capillary tube 400' in between, and the acoustic couplant 302 was distilled water.

The optically transparent portion 702 of the capillary tube 400' was centered and clamped between two shims 200 between the bodies 104, 106. Compression of the acoustic coupler 102' by an external clamp (not shown) permits the shim 200 to form a gasket-tight fit around the capillary. A microliter gas tight syringe 704 was attached to one end of the capillary tube 400' using a set of Microtight connectors (Upchurch, Oak Harbor Wash.) (not shown) in which an Upchurch F-185X microsleeve (not shown) is slipped over the 360 mm capillary tubing as an assembly and the assembly is inserted into a M-110 minitight Kel-F fitting (not shown) and tightened in a P-624 tefzel female luer (not shown).

The capillary tube 400' clamped in the center of the acoustic coupler 102' was centered in the excitation source (not shown) by adjusting the acoustic coupler 102' in the X-Y plane until the shadow of the capillary tube 400' as seen on an index card was centered in the beam 112.

Figure 8A:
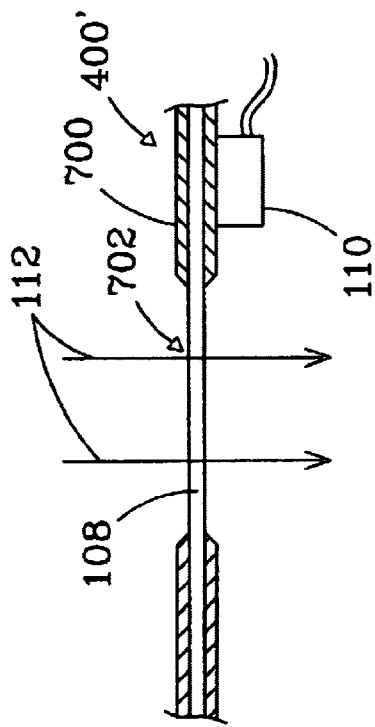
FIG. 8a is a section view of a test setup using a capillary tube with no acoustic coupler.

A first test was conducted to attempt to obtain an acoustic signal 114 from a sample 108 within a sample container 400, specifically a capillary tube 400', without both an acoustic couplant 302 and an acoustic coupler 102 as shown in FIG. 8a. The capillary tube 400' had a polyamide coating 700 and a portion 702 wherein the polyamide coating 700 was removed. The acoustic detector 110 was placed upon the capillary tube 400' a distance of 2–3 inches from the light beam 112 path. The acoustic detector 110 was located at a remote location to prevent a pyroelectric signal from direct absorption of the laser light 112.

The light beam 112 was passed through the capillary tube 400'. No acoustic signal 114 was observed at low laser powers (<microjoules/cm$^2$), and at higher laser powers (millijoules/cm$^2$) the sample 108 was irreversibly damaged. Even if an acoustic signal 114 could have been observed, the geometry was not conducive to dynamic signal processing.

Figure 8B:
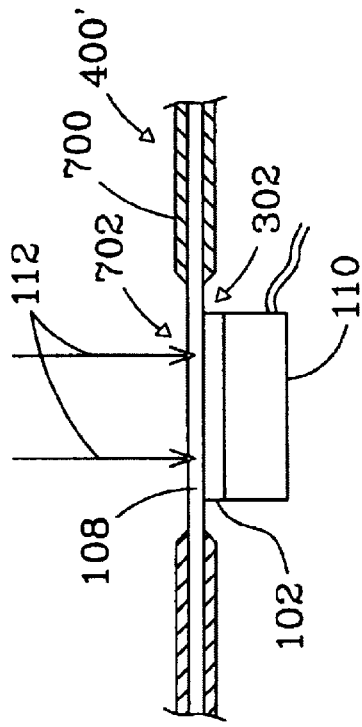
FIG. 8b is a section view of a test setup using a capillary tube and a reflector as the acoustic coupler.

In a second test, shown in FIG. 8b, an acoustic coupler 102 and acoustic couplant 302 were added to the setup. The acoustic coupler 102 was a dielectric mirror with the detector 110 mounted thereon. The acoustic couplant 302 was vacuum grease or water held by surface tension in the cusp between the capillary tube 400' and the acoustic coupler 102. The background signal was so large that additional signal processing would be needed to extract the sample signal.

EXAMPLE 1

An experiment was conducted to compare an inorganic liquid (benzene) to an inorganic liquid (water) for the acoustic couplant 302. Comparison of the acoustic waveforms obtained from irradiation of the PA standard, (OHB), using water and benzene as the acoustic couplant 302 provided two notable observations. First, when water was used as the acoustic couplant 302, the acoustic waveform arrived at the detector 70 ns before the acoustic waveform obtained when benzene was used as the acoustic couplant 302 because the velocity of sound in water is faster. Second, when water was used as the acoustic couplant 302, the amplitude of the acoustic waveform is 40% greater than the signal observed when the acoustic couplant 302 was benzene because of a better acoustic impedance match between water and quartz.

These results demonstrated acoustic wave propagation through the photoacoustic sample vessel.

EXAMPLE 2

An experiment was conducted to demonstrate that dynamic photoacoustic experiments are possible with the present invention and to demonstrate utility with different samples 108.

Benzophenone triplet quenching kinetics. For the dynamic studies, the 355 laser line was attenuated to provide ca. 28 mJ energy incident upon the sample 108. The energy absorbed ($H_{th}$) by the sample 108 was about 1000 nJ.

In the presence of potassium iodide (KI), the triplet excited state (Bp*$^3$) was quenched by an electron transfer mechanism to yield ground state Bp plus heat.

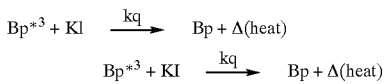

Figure 9:
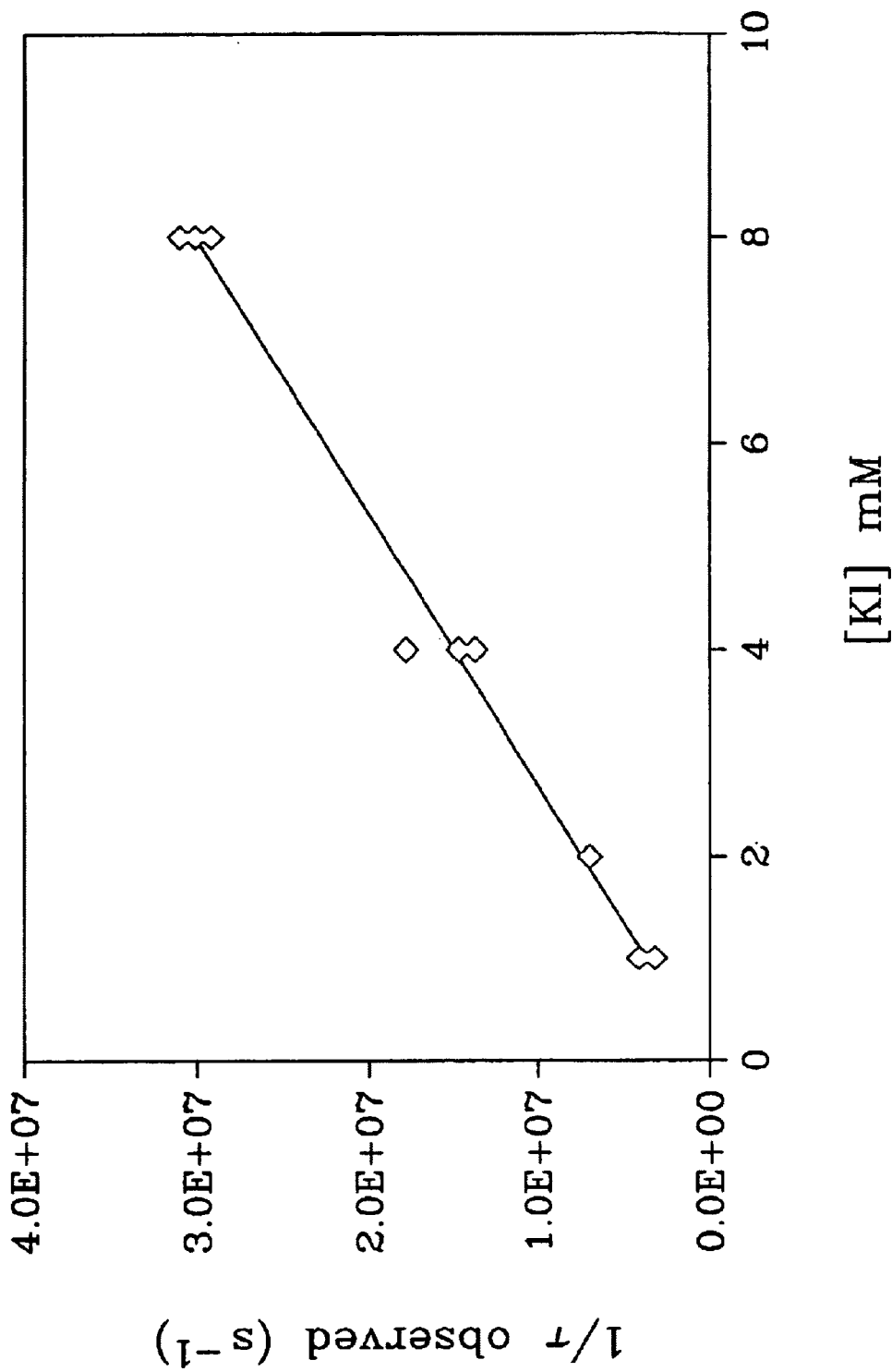
FIG. 9 is a plot of $1/\pi$ observed $BP^{*3}$ verses potassium iodide (KI) concentration.

As expected, addition of KI (1–8 mM) to the Bp sample decreased the observed lifetime ($1/\tau_{obs}$) of Bp*$^3$. The rate of triplet quenching calculated from the slope of a plot of $1/\tau_{obs}$ versus [KI] (FIG. 9). Linear regression yielded a quenching rate constant of $(3.9\pm0.2)\times10^9$ M$^{-1}$ s$^{-1}$ for Bp*$^3$ quenching by KI, which compares well with the literature value $4\times10^9$ M$^{-1}$ s$^{-1}$. By obtaining the dynamics from the photoacoustic signal the selectivity was significantly enhanced. For example, from the amplitude of the photoacoustic signal a concentration of the solute could be obtained if it was known to be benzophenone. Greater assurance that the solute was Bp may be obtained from the dynamics, the behavior of the photoacoustic signal as a function of its chemistry with a quencher. Few molecules would yield the same dynamic signal thus providing a method of selectivity. In addition, variable pressure capabilities provide a means to probe the dynamics of the photoacoustic signal to further enhance the selectivity of photoacoustic analysis.

Closure

While various embodiments of the present invention have been shown and described, it will be apparent to those skilled in the art that many changes and modifications may be made without departing from the invention in its broader aspects. The appended claims are therefore intended to cover all such changes and modifications as fall within the true spirit and scope of the invention.

It is claimed:

1. A photoacoustic sample vessel for analyzing a sample of between two nanoliters and 1 µl comprising:
   (a) an acoustic couplant selected from the group consisting of liquid, solid, and combinations thereof;
   (b) an acoustic coupler having a chamber capable of holding a sample having a volume of between two nanoliters and 1 µl and said acoustic couplant; and
   (c) an acoustic detector, wherein electromagnetic energy generates an acoustic signal within a portion of said sample having a volume of between two nanoliters and 1 µl, said acoustic signal propagates through said sample to and through said acoustic coupler to said acoustic detector.

2. The photoacoustic sample vessel as recited in claim 1, wherein said acoustic detector is mounted on said acoustic coupler so that said acoustic signal propagates through said sample to and through said acoustic couplant to and through said acoustic coupler to said acoustic detector.

3. A photoacoustic sample vessel for analyzing a sample of between two nanoliters and 1 µl comprising:

(a) an acoustic couplant selected from the group consisting of liquid, solid, and combinations thereof;

(b) an acoustic coupler having a chamber capable of holding a sample having a volume of between two nanoliters and 1 $\mu$l and said acoustic couplant; and (c) an acoustic detector, wherein electromagnetic energy generates an acoustic signal within a portion of said sample having a volume of between two nanoliters and 1 $\mu$l, wherein said acoustic detector is in contact with said acoustic couplant so that said acoustic signal propagates through said sample to and through said acoustic couplant directly to said acoustic detector.

4. The photoacoustic sample vessel as recited in claim 1, further comprising a sample container, wherein said sample is contained within said sample container and said acoustic signal propagates through said sample to and through a wall of said sample container to and through said acoustic couplant, to and through said acoustic coupler, to said acoustic detector.

5. The photoacoustic sample vessel as recited in claim 4, wherein said sample is pressurized within said sample container above atmospheric pressure.

6. The photoacoustic sample vessel as recited in claim 4, wherein said sample container comprises a capillary tube.

7. The photoacoustic sample vessel as recited in claim 6, wherein said sample is pressurized within said capillary tube above atmospheric pressure.

8. A method of photoacoustically analyzing a sample of between two nanoliters and 1 $\mu$l comprising the steps of:

(a) placing a sample of between two nanoliters and 1 $\mu$l and an acoustic couplant into a chamber provided by an acoustic coupler, said acoustic couplant selected from the group consisting of liquid, solid, and combinations thereof;

(b) passing electromagnetic energy through said sample and generating an acoustic signal within a portion of said sample having a volume of between two nanoliters and 1 $\mu$l, that propagates through the portion of said sample having a volume of between two nanoliters and 1 $\mu$l to and through said acoustic coupler to an acoustic detector.

9. The method as recited in claim 8, further comprising the step of pressurizing said sample above atmospheric pressure.

10. The method as recited in claim 8, wherein said sample is contained within a sample container so that said acoustic signal propagates through said sample to and through the wail of said sample container to and through said acoustic couplant, to and through said acoustic coupler, to said acoustic detector.

11. The method as recited in claim 10, further comprising the step of pressurizing said sample at a pressure less than a burst pressure of said sample container.

12. The method as recited in claim 10, wherein said sample container comprises a capillary tube.

* * * * *